Figure 1:
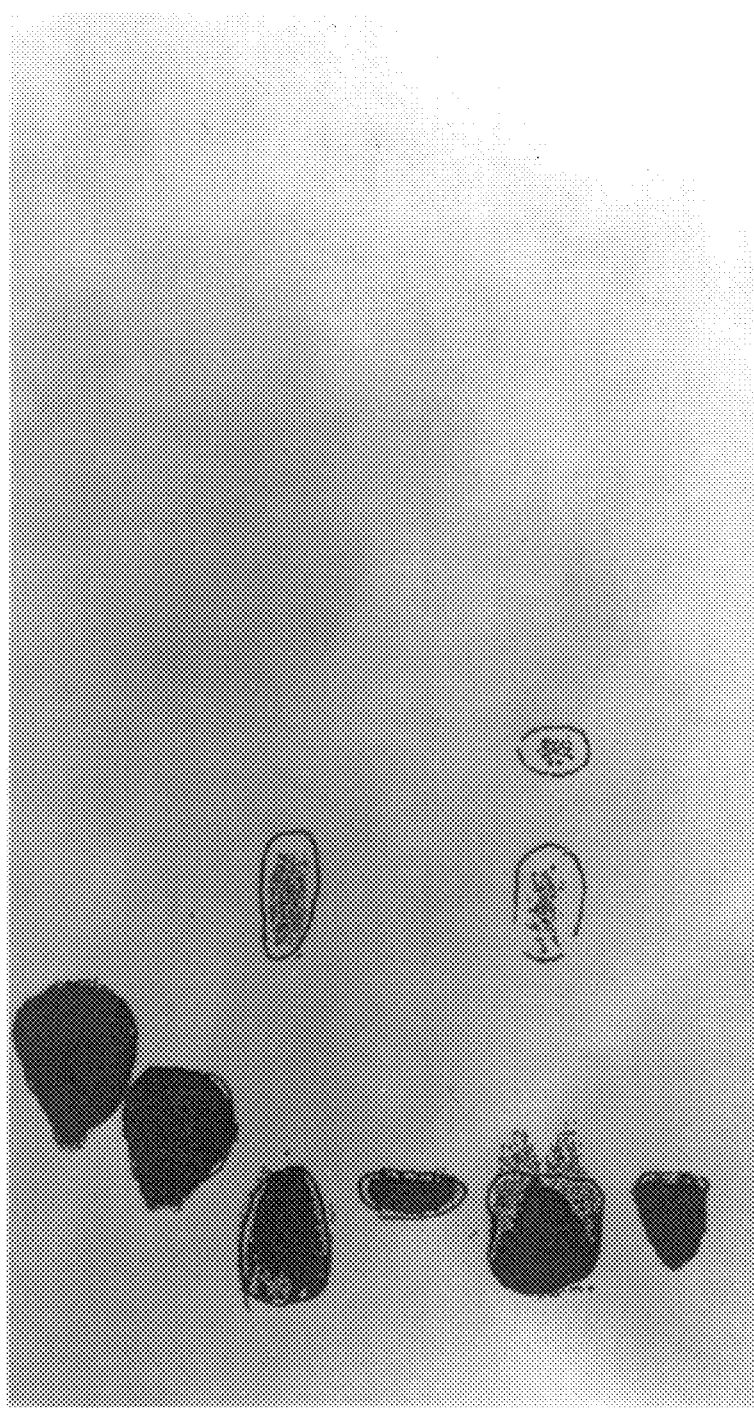

United States Patent [19]
Eisenbach-Schwartz et al.

[11] Patent Number: 6,126,939
[45] Date of Patent: Oct. 3, 2000

[54] ANTI-INFLAMMATORY DIPEPTIDE AND PHARMACEUTICAL COMPOSITION THEREOF

[75] Inventors: Michal Eisenbach-Schwartz, Rehovot; Pierre Beserman, Moshav Satarya, both of Israel; David L. Hirschberg, Menlo Park, Calif.

[73] Assignee: Yeda Research and Development Co. Ltd., Rehovot, Israel

[21] Appl. No.: 08/864,301

[22] Filed: May 28, 1997

Related U.S. Application Data

[63] Continuation-in-part of application No. 08/753,141, Nov. 20, 1996.
[60] Provisional application No. 60/025,376, Sep. 3, 1996, and provisional application No. 60/031,191, Nov. 20, 1996, abandoned.
[51] Int. Cl.$^7$ .......................... A61K 38/05; A61K 51/08; C07K 5/06
[52] U.S. Cl. .................. 424/185.1; 514/19; 530/300; 562/560
[58] Field of Search ...................... 530/300; 260/998.22; 514/19; 424/185.1; 562/560

[56] References Cited

U.S. PATENT DOCUMENTS

| | | |
|---|---|---|
| 4,244,946 | 1/1981 | Rivier et al. . |
| 4,305,872 | 12/1981 | Johnston et al. . |
| 4,316,891 | 2/1982 | Guillemin et al. . |
| 5,455,279 | 10/1995 | Lipton . |
| 5,506,231 | 4/1996 | Lipton . |
| 5,510,329 | 4/1996 | Belkin et al. . |

FOREIGN PATENT DOCUMENTS

| | | |
|---|---|---|
| WO 84/00108 | 1/1984 | WIPO . |
| WO 86/04334 | 7/1986 | WIPO . |
| WO 94/24154 | 10/1994 | WIPO . |
| WO 95/03067 | 2/1995 | WIPO . |

OTHER PUBLICATIONS

BACHEM Biochemica GmbH, Catalog Peptides and Biochemica, 1996, pp. 78–81, 84, 85, 90, 91, 386, 387, 426, 427, 480, 481, 638, 639, 780, 781, 814 and 815.
Chem. Abs., 1993, 119(9):93494, Cheido, M. et al., 1993, "Peptide modulation of immune responses", Eksp. Klin. Farmakol. 56(1):51 and an English language translation thereof.
Auriault et al., 1985, "Regulatory Role of a Tripeptide (TKP) from the Second Constant Domain of Immunoglobulin G–I. Inhibition of Rat and Human Macrophage Activities", Int. J. Immunopharmac. 7:73–79.
Beserman et al., 1995, "Discovery of a Brain–Derived Peptide, which Provides a Biochemical Basis for Immune Privilege and the Evolutionary Loss of CNS Regeneration", Soc. Neurosci. 21.
Bump et al., 1990, "The Characteristics of Purified HL60 Tuftsin Receptors", Mol. Cell. Biochem. 92:77–84.
Calcutt et al., 1994, "Inhibition of Macrophage Chemotaxis and Peripheral Nerve Regeneration in Normal and Hyperglycemic Rats by the Aldose Reductase Inhibitor Tolrestat", Exp. Neurol. 128:226–232.
Cheido et al., 1993, "Peptide Modulation of Immune Responses", Eksp. Klin. Farmakol. 56:51.
Fridkin et al., 1989, "Tuftsin: Its Chemistry, Biology, and Clinical Potential", Crit. Rev. Biochem. Mol. Bio. 24:1–40.
Gilat et al., 1994, "Regulation of Adhesion of CD4$^+$ T Lymphocytes to Intact or Heparinase–Treated Subendothelial Extracellular Matrix by Diffusible or Anchored RANTES and MIP–1β", J. Immunol. 153:4899–4906.
Himmi et al., 1985, "Regulatory Role of a Peptide from the Second Constant Domain of Immunoglobulin G–II. In Vitro effect on Granuloma Formation around *S. Mansoni* Eggs ", Int. J. Immunopharm. 7:231–237.
Hirschberg and Schwartz, 1995, "Macrophage Recruitment to Acutely Injured Central Nervous System Is Inhibited by a Resident Factor: A Basis for an Immune–Brain Barrier", J. Neuroimmunol. 61:89–96.
Kolata, 1985, "Avoiding the Schistosome's Tricks", Science 227:285–287.
Lotan and Schwartz, 1994, "Cross Talk Between the Immune System and the Nervous System in Response to Injury: Implications for Regeneration", FASEB J. 8:1026–1033.
Marki et al., 1981, "Total Solid–Phase Synthesis of Porcine Gut Gastrin Releasing Pepide (GRP), a Mammalian Bombesin", J. Am. Chem. Soc. 103:3178–3185.
Mathur et al., 1977, "Antilipolytic Activity of Some Arginine Peptides", Indian J. Biochem. Biophys. 14:384–385.

(List continued on next page.)

Primary Examiner—Christina Y. Chan
Assistant Examiner—Amy DeCloux
Attorney, Agent, or Firm—Browdy and Neimark

[57] ABSTRACT

The present invention is directed to peptides of the formulas (i) Xaa-Yaa-Arg, wherein either Xaa is any amino acid residue and Yaa is Glu or Xaa is absent and Yaa is any amino acid residue with the exception of Pro; (ii) Arg-Yaa-Xaa, wherein either Xaa is any amino acid residue and Yaa is Glu or Xaa is absent and Yaa is any amino acid residue with the exception of Asn; (iii) Xaa-Arg-Yaa, wherein Xaa is any amino acid residue and Yaa is Glu; and (iv) Yaa-Arg-Xaa, wherein Xaa is any amino acid residue and Yaa is Glu, and to derivatives thereof, which exert an inhibitory effect on macrophage migration and/or macrophage phagocytic activity. In addition, the peptides and derivatives thereof exert an inhibitory effect on the ability of macrophages and T cells to adhere to extracellular matrix and/or fibronectin. The peptides and derivatives thereof exert an inhibitory effect on a humoral and/or cellular immune response. The invention is also directed to methods for use of the peptides and derivatives thereof and compositions containing them for the inhibition of inflammation, including but not limited to, inflammation at a joint, in the central nervous system generally, at specific lesions in the central nervous system, and other immune privileged sites.

4 Claims, 5 Drawing Sheets

OTHER PUBLICATIONS

Mathur et al., 1980, "Synthesis & Hypoglycemic Activity of Arginine Peptides", Indian J. Biochem. Biophys 14:303–305.

Merrifield, 1964, "Solid Phase Peptide Synthesis. I. The Synthesis of a Tetrapeptide", J. Am. Chem. Soc. 85:2149–2154.

Nishioka et al., 1973, "Characteristics and Isolation of the Phagocytosis–Stimulating Peptide, Tuftsin", Biochem. Biophys. Acta 310:217–228.

Ouaissi et al., 1986, "Trypanosoma cruzi Infection Inhibited by Peptides Modeled from a Fibronectin Cell Attachment Domain", Science 10:603–607.

Plata–Salaman, 1989, "Immunomodulators and Feeding Regulation: A Humoral Link Between the Immune and Nervous Systems", Brain Behav. Immunol. 3:193–213.

Schwartz et al., 1996, "Optic Nerve Disease and Injury: Prospects for Induction of Regeneration", Prog. Ret. Eye Res. 15:569–582.

Siemion et al., 1990, "The Analgesic Activity of Some Kyotorphin–Tuftsin Analogs", Pol. J. Pharmacol. Pharm. 42:177–184.

Siemion et al., 1991, "The Evidence on the Possible Interleukin–1α Tuftsin Competition", Arch. Immunol. Ther. Exp. 39:605–611.

Sigma Chemical Catalogue, 1995, pp. 132–135, 496, 497, 788, 981, and 1102.

Thanos et al., 1993, "Treatment of the Adult Retina with Microglia–Suppressing Factors Retards Axotomy–Induced Neuronal Degradation and Enhances Axonal Regeneration in Vivo and In Vitro", J. Neurosci. 13:455–466.

Thanos et al., 1996, "Retinal Microglia", Prog. Ret. Eye Res. 15:331–361.

Tzehoval et al., 1978, "Tuftsin (an Ig–Associated Tetrapeptide) Triggers the Immunogenic Function of Macrophages: Implications for Activation of Programmed Cells", Proc. Natl. Acad. Sci USA 75:3400–3404.

Vale et al., 1981, "Chracterization of a 41–Residue Ovine Hypothalamic Peptide that Stimulates Secretion of Corticotropin and β–Endorphin", Science 213:1394–1397.

Wagle et al., 1989, "Specific Translocation of Tuftsin (Thr–Lys–Pro–Arg), a Natural Immunomodulating Peptide, into the Nuclei of Human Monocytes", Biochem. Biophys. Rev. Commun. 159:1147–1153.

Weber et al., 1971, "Merrifield–Synthesen variierter A–Ketten unter Verwendung verschiedener S–Alkylmercapto–Schutzgruppen", Hoppe–Seyler's Z. Physiol. Chem. 352:419–429.

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: peptide
      derivative

<400> SEQUENCE: 1

Glu Arg Glu Arg
```

ANTI-INFLAMMATORY DIPEPTIDE AND PHARMACEUTICAL COMPOSITION THEREOF

The present invention claims priority benefits of copending U.S. provisional patent application Ser. No. 60/025,376, filed Sep. 3, 1996 and copending U.S. provisional application Ser. No. 60/031,191, filed Nov. 20, 1996. The present invention is a continuation-in-part of U.S. patent application Ser. No. 08/753,141, filed Nov. 20, 1996, now abandoned which is incorporated by reference herein in its entirety.

TABLE OF CONTENTS
1. FIELD OF THE INVENTION
2. BACKGROUND OF THE INVENTION
3. SUMMARY OF THE INVENTION
4. BRIEF DESCRIPTION OF THE FIGURES
5. DETAILED DESCRIPTION OF THE INVENTION
   5.1. PEPTIDES AND PEPTIDE DERIVATIVES USEFUL AS ANTI-INFLAMMATORY AND ANTI-IMMUNE RESPONSE AGENTS
   5.2. METHODS AND COMPOSITIONS FOR TREATING OR AMELIORATING INFLAMMATION OR FOR INHIBITING AN IMMUNE RESPONSE
6. EXAMPLE: MIGRATION PATTERN OF IMMUNE PRIVILEGE FACTOR AND PEPTIDE GLU-ARG IS THE SAME
7. EXAMPLE: DELAY IN ONSET AND REDUCTION OF SEVERITY AND INCIDENCE OF ACUTE EXPERIMENTAL ACUTE ENCEPHALITIS
8. EXAMPLE: INHIBITION OF T CELL ADHESION
9. EXAMPLE: REDUCTION IN SEVERITY OF LPS-INDUCED UVEITIS BY PEPTIDE GLU-ARG

1. FIELD OF THE INVENTION

The present invention is directed to peptides which have macrophage and/or T cell inhibitory activities and thus, anti-inflammatory activity. The present invention is also directed to methods for the use of the peptides and pharmaceutical compositions containing a peptide in the modulation of immune responses, i.e., a humoral and/or cellular immune response, including, but not limited to, an immune response accompanying inflammation associated with or caused by disease.

2. BACKGROUND OF THE INVENTION

Citation or identification of any reference in Section 2 or any other section of this application shall not be construed as an admission that such reference is available as prior art to the present invention.

A classical inflammatory response is characterized by the invasion of monocyte cells into the afflicted tissue within hours after injury. Among these early invaders are macrophages capable of mediating a myriad of functions, from removal of debris and dead cells and dying tissue by phagocytosis to secretion of enzymes and growth factors that facilitate tissue regeneration. Macrophage-derived cytokines, such as platelet-derived growth factor (PDGF), tumor necrosis factor alpha (TNFα), transforming growth factor beta (TGFβ1), heparin-binding epidermal growth factor (HB-EGF), interleukin-1 (IL-1) and interleukin-6 (IL-6), have been shown to have secondary effects on other bone marrow derived cells and on resident cells in the injured tissue.

Several factors are known which modulate macrophage activity. For example, tuftsin, a derivative of IgG, is a potent macrophage stimulator. Interferon-γ and Tumor Necrosis Factor are also potent stimulators. There are also factors which inhibit macrophage activity, called MIFs. For example, a tripeptide, Thr-Lys-Pro, TKP, a synthetic derivative of tuftsin, has been shown to inhibit macrophage migration and reduce secretion of IL-1 macrophages (see Nishioka et al., 1973, Biochem. Biophys. Acta 310:217–228; Bump et al., 1990, Mol. Cell, Biochem. 92:77–84; Fridkin et al., 1989, Crit. Rev. Biochem. Mol. Bio. 24:1–40; Tzehoval et al., 1978. Proc. Natl. Acad. Sci. USA 75:3400–3404; Thanos et al., 1993, J. Neurosci. 13:455–466; Plata-Salaman, 1989, Brain Behav. Immunol. 3:193–213; Wagle et al., 1989, Biochem. Biophys. Rev. Commun. 159:1147–1153; Sienion et al., 1991, Arch. Immunol. Ther. Exp. 39:605–611; Auriault et al., 1985, Immunopharmac. 7:73–79). Another MIF is Tolrestat, an aldose reductase inhibitor (Calcott et al., 1994, Exp. Neurol. 128:226–232).

Mathur and Kishore, 1980,Indian J. Biochem. Biophys. 17:303–305, demonstrated that i.p. administration of 100 mg/kg of a certain peptide and certain peptide derivatives containing arginine into rats resulted in the lowering of blood sugar levels, i.e., the peptides have hypoglycemic activity. The peptides tested having hypoglycemic activity are Arg-Asn, Arg-Asn-$NH_2$, Asn-Arg-$NH_2$, Gln-Arg-OMe, Gln-Arg-$NH_2$, and Glu-Arg-OMe. The peptide Glu-Arg-$NH_2$ was also tested but did not significantly lower blood sugar levels.

Mathur et al., 1977, Indian J. Biochem. Biophys. 14:384–385, demonstrated that the following peptide derivatives have antilipolytic activity as measured in an in vitro test assay: Arg-Asn-$NH_2$, Asn-Arg-$NH_2$, Gln-Arg-$NH_2$, Glu-Arg-OMe, and Glu-Arg-$NH_2$. Arg-Asn and Gln-Arg-OMe were tested but showed no significant antilipolytic activity.

3. SUMMARY OF THE INVENTION

The present invention is directed to peptides and derivatives thereof and compositions comprising them, which have macrophage inhibitory and/or T cell inhibitory activity and thus, anti-inflammatory activity. The peptides and derivatives thereof have anti-immune activity, i.e., inhibitory effects against a cellular and/or humoral immune response, including a response not associated with inflammation. The peptides and derivatives thereof also inhibit the ability of macrophages and T cells to adhere to extracellular matrix components and fibronectin, as well as upregulate fas receptor expression in T cells.

The present invention is based, at least in part, on the discovery that peptides of the formulas (i) Xaa-Yaa-Arg, wherein either Xaa is any amino acid residue and Yaa is Glu or Xaa is absent and Yaa is any amino acid residue with the exception of Pro; (ii) Arg-Yaa-Xaa, wherein either Xaa is any amino acid residue and Yaa is Glu or Xaa is absent and Yaa is any amino acid residue with the exception of Pro; (iii) Xaa-Arg-Yaa, wherein Xaa is any amino acid residue and Yaa is Glu; and (iv) Yaa-Arg-Xaa, wherein Xaa is any amino acid residue and Yaa is Glu, exhibit inhibitory activity on macrophage migration and/or on macrophage phagocytic activity.

The present invention thus relates to a substantially pure anti-inflammatory peptide or a peptide derivative selected from the group consisting of: (i) a peptide of the amino acid sequence: Xaa-Yaa-Arg wherein either Xaa is any amino acid residue and Yaa is Glu or Xaa is absent and Yaa is any amino acid residue with the exception of Pro; (ii) a peptide of the amino acid sequence: Arg-Yaa-Xaa wherein either Xaa is any amino acid residue and Yaa is Glu or Xaa is absent and Yaa is any amino acid residue with the exception of Asn; (iii) a peptide of the amino acid sequence: Xaa-Arg-Yaa wherein Xaa is any amino acid residue and Yaa is Glu; (iv) a peptide of the amino acid sequence: Yaa-Arg-Xaa wherein Xaa is any amino acid residue and Yaa is Glu; (v) a cyclic derivative of a peptide of formula (i) to (iv); (vi) a peptide selected from a peptide of formula (i) to (v), Pro-Arg and Arg-Asn, in which peptide one or more amino acid residues have been replaced by the corresponding D-isomer or by a non-natural amino acid residue; (vii) a chemical derivative of a peptide selected from a peptide of formula (i) to (vi), Pro-Arg and Arg-Asn, but excluding the derivatives Arg-Asn-$NH_2$, Asn-Arg-$NH_2$, Gln-Arg-$NH_2$, Glu-Arg-$NH_2$, Gln-Arg-OMe, and Glu-Arg-OMe; (viii) a dual peptide consisting of two the same or different peptides selected from the peptides and derivatives (i) to (vii), Pro-Arg and Arg-Asn, wherein the peptides or derivatives are covalently linked to one another either directly or through a spacer; and (ix) a multimer comprising a number of the same or different peptides selected from the peptides and derivatives (i) to (vii), Pro-Arg and Arg-Asn.

According to the invention, an anti-inflammatory dipeptide as in (i) above is selected from the group consisting of: Ala-Arg, Arg-Arg, Asn-Arg, Asp-Arg, Cys-Arg, Gln-Arg, Glu-Arg, Gly-Arg, His-Arg, Ile-Arg, Leu-Arg, Lys-Arg, Met-Arg, Phe-Arg, Ser-Arg, Thr-Arg, Trp-Arg, Tyr-Arg and Val-Arg. An anti-inflammatory tripeptide as in (i) above is selected from the group consisting of: Ala-Glu-Arg, Arg-Glu-Arg, Asn-Glu-Arg, Asp-Glu-Arg, Cys-Glu-Arg, Gln-Glu-Arg, Glu-Glu-Arg, Gly-Glu-Arg, His-Glu-Arg, Ile-Glu-Arg, Leu-Glu-Arg, Lys-Glu-Arg, Met-Glu-Arg, Phe-Glu-Arg, Pro-Glu-Arg, Ser-Glu-Arg, Thr-Glu-Arg, Trp-Glu-Arg, Tyr-Glu-Arg and Val-Glu-Arg.

An anti-inflammatory dipeptide as in (ii) above is selected from the group consisting of: Arg-Ala, Arg-Asp, Arg-Cys, Arg-Gln, Arg-Glu, Arg-Gly, Arg-His, Arg-Ile, Arg-Leu, Arg-Lys, Arg-Met, Arg-Phe, Arg-Pro, Arg-Ser, Arg-Thr, Arg-Trp, Arg-Tyr and Arg-Val. An anti-inflammatory tripeptide as in (ii) above is selected from the group consisting of: Arg-Glu-Ala, Arg-Glu-Asn, Arg-Glu-Asp, Arg-Glu-Cys, Arg-Glu-Gln, Arg-Glu-Glu, Arg-Glu-Gly, Arg-Glu-His, Arg-Glu-Ile, Arg-Glu-Leu, Arg-Glu-Lys, Arg-Glu-Met, Arg-Glu-Phe, Arg-Glu-Pro, Arg-Glu-Ser, Arg-Glu-Thr, Arg-Glu-Trp, Arg-Glu-Tyr and Arg-Glu-Val.

An anti-inflammatory tripeptide as in (iii) is selected from the group consisting of: Ala-Arg-Glu, Arg-Arg-Glu, Asn-Arg-Glu, Asp-Arg-Glu, Cys-Arg-Glu, Gln-Arg-Glu, Glu-Arg-Glu, Gly-Arg-Glu, His-Arg-Glu, Ile-Arg-Glu, Leu-Arg-Glu, Lys-Arg-Glu, Met-Arg-Glu, Phe-Arg-Glu, Pro-Arg-Glu, Ser-Arg-Glu, Thr-Arg-Glu, Trp-Arg-Glu, Tyr-Arg-Glu and Val-Arg-Glu.

An anti-inflammatory tripeptide as in (iv) above is selected from the group consisting of: Glu-Arg-Ala, Glu-Arg-Arg, Glu-Arg-Asn, Glu-Arg-Asp, Glu-Arg-Cys, Glu-Arg-Gln, Glu-Arg-Gly, Glu-Arg-His, Glu-Arg-Ile, Glu-Arg-Leu, Glu-Arg-Lys, Glu-Arg-Met, Glu-Arg-Phe, Glu-Arg-Pro, Glu-Arg-Ser, Glu-Arg-Thr, Glu-Arg-Trp, Glu-Arg-Tyr and Glu-Arg-Val.

In a preferred embodiment of the invention, the peptide is Glu-Arg.

The term "peptide derivative" as used throughout the specification and claims herein is intended to include the derivatives defined in (v) to (ix) above, namely cyclic peptides, peptides obtained by substitution of a natural amino acid residue by the corresponding D-stereomer or by a non-natural amino acid residue, chemical derivatives of the peptides, dual peptides and multimers of the peptides.

The present invention is also directed to pharmaceutical compositions comprising a pharmaceutically acceptable carrier and an anti-inflammatory peptide or peptide derivative of the invention. In a preferred embodiment, the composition contains the peptide Glu-Arg as the active ingredient.

The present invention is further directed to pharmaceutical compositions comprising a pharmaceutically acceptable carrier and a peptide or peptide derivative selected from the group consisting of an anti-inflammatory peptide or peptide derivative as defined above, the peptide Pro-Arg or a derivative thereof, and the peptide Arg-Asn or a derivative thereof, which composition inhibits macrophage activity and has macrophage migration and/or macrophage phagocytic inhibitory activity as assessed in an in vitro assay.

The present invention is still further directed to pharmaceutical compositions comprising a pharmaceutically acceptable carrier and a peptide or peptide derivative selected from the group consisting of an anti-inflammatory peptide or peptide derivative as defined above, the peptide Pro-Arg or a derivative thereof, and the peptide Arg-Asn or a derivative thereof, which composition inhibits T cell activity and has T cell inhibitory activity as assessed in an in vitro assay.

In the following description and claims whenever the expression "the peptides, peptide derivatives and compositions of the invention" is used with respect to pharmaceutical compositions which either inhibit macrophage activity and have macrophage migration and/or macrophage phagocytic inhibitory activity or inhibit T cell activity and have T cell inhibitory activity, both activities as assessed in an in vitro assay, or such expression is used with reference to the methods of treatment disclosed herein, it is to be understood that said expression refers to "a peptide or peptide derivative selected from the group consisting of an anti-inflammatory peptide or peptide derivative as defined herein at page 3, line 28 through page 5, line 19, the peptide Pro-Arg or a derivative thereof, and the peptide Arg-Asn or a derivative thereof, wherein the derivatives of Pro-Arg and Arg-Asn include the derivatives as defined herein at page 4, lines 4–19 and page 5, lines 22–28.

The present invention is also directed to compositions comprising a peptide or peptide derivative together with a pharmaceutically acceptable carrier. The pharmaceutical compositions are used as inhibitors of macrophage migration and/or macrophage phagocytic activity and inflammation in animals, preferably mammals, including humans.

The pharmaceutical compositions are also used as inhibitors of macrophage and T cell adhesive activity in animals, preferably mammals, including humans. In one embodiment, the pharmaceutical compositions are used for their non-steroidal anti-inflammatory activity, i.e., anti-inflammatory, analgesic and anti-pyretic activities.

The present invention is also directed to methods of use of the peptides, peptide derivatives or compositions comprising a peptide or peptide derivative for the inhibition of macrophage migration and/or macrophage phagocytic activity and inflammation in animals, preferably mammals, including humans. The present invention is also directed to methods of use of said peptides, peptide derivatives or compositions comprising said peptide or peptide derivative for the inhibition of macrophage and T cell adhesive activity in animals, preferably mammals, including humans. The present invention is also directed to methods of use of said peptides, peptide derivatives or compositions comprising said peptide or peptide derivative for the inhibition of an immune response not associated with inflammation. The present invention is further directed to methods of use of the peptides, peptide derivatives or compositions comprising a peptide or peptide derivative for the restoration of immune privilege at immune privileged sites.

The peptides, peptide derivatives and pharmaceutical compositions of the present invention are used in the treatment of or amelioration of inflammatory symptoms in any disease, condition or disorder where immune and/or inflammation suppression would be beneficial. Inflammatory diseases, conditions or disorders in which the peptides, peptide derivatives and compositions of the present invention can be used to inhibit unwanted immune reactions and inflammation include, but are not limited to, arthritis, including but not limited to rheumatoid arthritis, and other diseases, conditions or disorders of the joints or musculoskeletal system in which immune and/or inflammation suppression would be beneficial.

The peptides, peptide derivatives and compositions are also useful to treat or ameliorate inflammation associated with hypersensitivity; allergic reactions; asthma; systemic lupus erythematosus; collagen diseases and other autoimmune diseases, conditions or disorders in which immune and/or inflammation suppression would be beneficial.

Moreover, the peptides, peptide derivatives and compositions are also useful to treat or ameliorate inflammation associated with atherosclerosis; arteriosclerosis; atherosclerotic heart disease; reperfusion injury; cardiac arrest; myocardial infarction; vascular inflammatory disorders; respiratory distress syndrome and other cardiopulmonary diseases, conditions or disorders where immune and/or inflammation suppression would be beneficial.

In addition, the peptides, peptide derivatives and compositions are also useful to treat or ameliorate inflammation associated with peptic ulcer; ulcerative colitis and other diseases, conditions or disorders of the gastrointestinal tract where immune inflammation suppression would be beneficial; hepatic fibrosis; liver cirrhosis and other hepatic diseases, conditions or disorders where immune and/or inflammation suppression would be beneficial; thyroiditis and other glandular diseases, conditions or disorders where immune and/or inflammation suppression would be beneficial; glomerulonephritis and other renal and urologic diseases, conditions or disorders where immune and/or inflammation suppression would be beneficial.

The peptides, peptide derivatives and compositions are also useful to treat or ameliorate inflammation associated with otitis and other otorhinolaryngological diseases, conditions or disorders where immune and/or inflammation suppression would be beneficial; dermatitis and other dermal diseases, conditions or disorders where immune and/or inflammation suppression would be beneficial; periodontal diseases and other dental diseases, conditions or disorders where immune and/or inflammation suppression would be beneficial.

Further, the peptides, peptide derivatives and compositions are also useful to treat or ameliorate inflammation associated with orchitis and epididimo-orchitis; infertility; orchidal trauma and other immune-related esticular diseases, conditions or disorders where immune and/or inflammation suppression would be beneficial; placental dysfunction; placental insufficiency; habitual abortion; eclampsia; preeclampsia and other immune and/or inflammatory-related gynecological diseases, conditions or disorders where immune and/or inflammatory suppressions would be beneficial.

In addition, the peptides, peptide derivatives and compositions are also useful to treat or ameliorate inflammation associated with posterior uveitis; intermediate uveitis; anterior uveitis; conjunctivitis; chorioretinitis; uveoretinitis; optic neuritis; intraocular inflammation, such as retinitis and cystoid macular edema; sympathetic ophthalmia; scleritis; retinitis pigmentosa; immune and inflammatory components of degenerative fondus disease; inflammatory components of ocular trauma; ocular inflammation caused by infection; proliferative vitreoretinopathies; acute ischemic optic neuropathy; excessive scarring, for example, following glaucoma filtration operation; immune and/or inflammation reaction against ocular implants and other immune and inflammatory-related ophthalmic diseases, conditions or disorders where immune and/or inflammation suppression would be beneficial.

Moreover, the peptides, peptide derivatives and compositions are also useful to treat or ameliorate inflammation associated with autoimmune diseases and conditions or disorders where, both in the central nervous system (CNS) and in any other organ, immune and/or inflammation suppression would be beneficial; Parkinson's disease; complications and/or side effects from treatment of Parkinson's disease; AIDS-related dementia complex (HIV-related encephalopathy); Devic's disease; Sydenham chorea; Alzheimer's disease and other degenerative diseases, conditions or disorders of the central nervous system where immune and/or inflammation suppression would be beneficial; inflammatory components of strokes; post-polio syndrome; immune and inflammatory components of psychiatric disorders; myelitis; encephalitis; subacute sclerosing panencephalitis; encephalomyelitis; acute neuropathy; subacute neuropathy; chronic neuropathy; Guillaim-Barre syndrome; Sydenham chorea; myasthenia gravis; pseudotumor cerebri; Down's Syndrome; Huntington's disease; amyotrophic lateral sclerosis; inflammatory components of central nervous system (CNS) compression or CNS trauma or infections of the CNS; inflammatory components of muscular atrophies and dystrophies; and immune and inflammatory related diseases, conditions or disorders of the central and peripheral nervous systems where immune and/or inflammation suppression would be beneficial.

In addition, the peptides, peptide derivatives and compositions are also useful to treat or ameliorate inflammation associated with post-traumatic inflammation; septic shock; infectious diseases where immune and/or inflammation suppression would be beneficial; inflammatory complications and side effects of surgery where immune and/or inflammation suppression would be beneficial; bone marrow transplantation and other transplantation complications and/or side effects where immune and/or inflammation suppression would be beneficial; inflammatory and/or immune complications and side effects of gene therapy, e.g., due to infection with a viral carrier; and inflammation associated with acquired immune deficiency syndrome (AIDS).

Further, the peptides, peptide derivatives and compositions are also useful to inhibit macrophage or T cell associated aspects of an immune response that are not associated with inflammation. The peptides, peptide derivatives and compositions are able to inhibit macrophage or T cell activities including, but not limited to, macrophage antigen-presenting activity, macrophage cytokine production, T cell cytokine production, T cell adhesion activity, T cell proliferation, etc. Thus, the peptides, peptide derivatives and compositions are useful to suppress or inhibit a humoral and/or cellular immune response.

The peptides, peptide derivatives and compositions are also useful to treat or ameliorate monocyte and leukocyte proliferative diseases, e.g., leukemia, by reducing the amount of monocytes and lymphocytes.

The peptides, peptide derivatives and pharmaceutical compositions of the invention are further useful for the prevention and/or treatment of graft rejection in cases of transplantation of natural or artificial cells, tissue and organs, such as cornea, bone marrow, organs, lenses, pacemakers, natural and artificial skin tissue, and the like.

In yet another embodiment, the peptides, peptide derivatives and compositions of the invention are useful to restore immune privilege at an immune privileged site which has lost its immune privilege such as brain, eye and testis.

4. BRIEF DESCRIPTION OF THE FIGURES

FIG. 1 is a photograph of a thin-layer chromatography (TLC) plate showing the migration pattern of glutamic acid (Lane 1), arginine (Lane 2), purified immune privilege factor (Lane 3), peptide Glu-Arg after lyophilization (Lane 4), enriched immune privilege factor (Lane 5), and Glu-Arg before lyophilization (Lane 6). See text, Section 6, for details.

Figure 2:
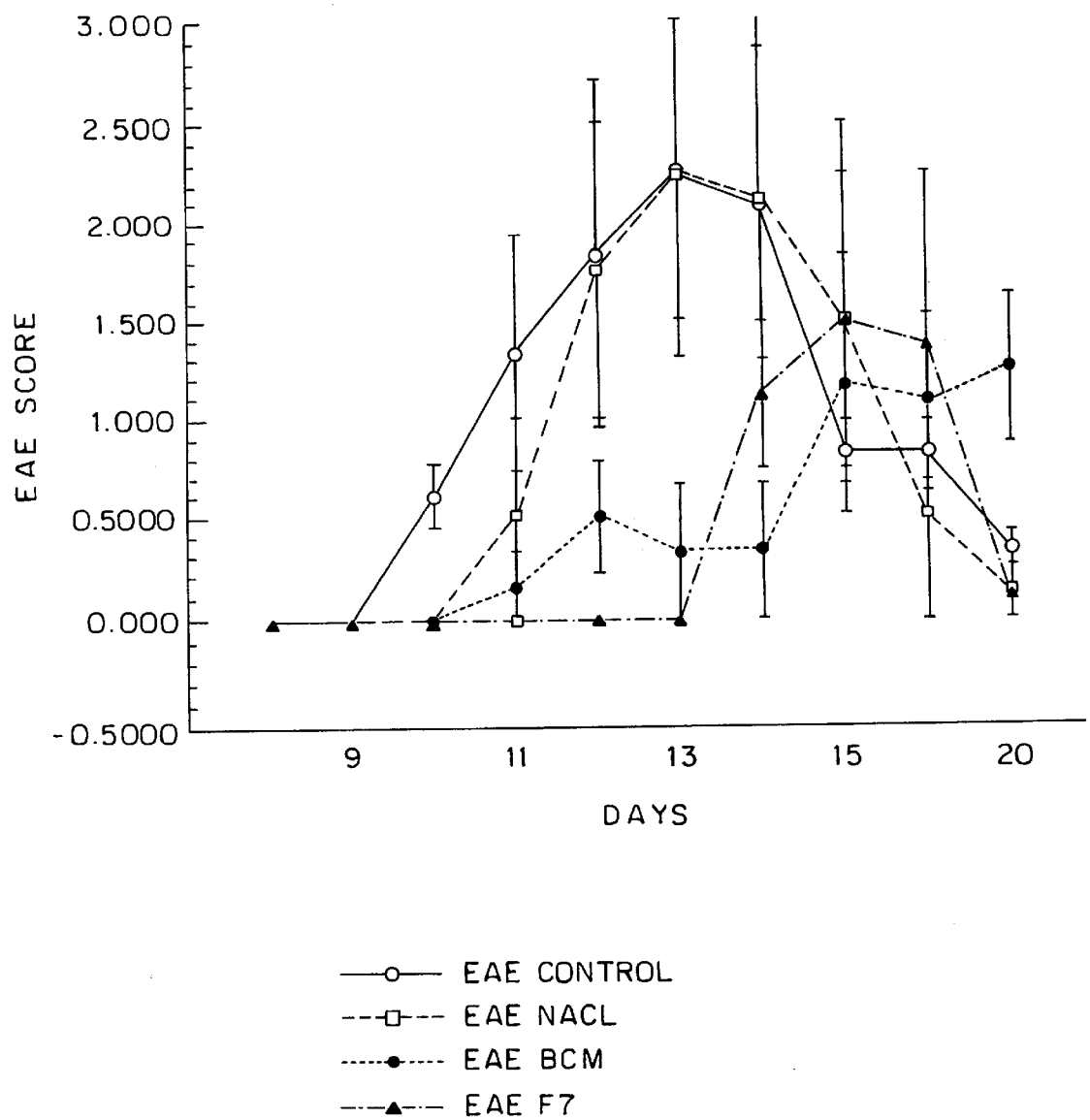

FIG. 2 is a graph showing the effect of saline (NaCl 0.9%) (EAE NACL), brain-conditioned medium (EAE BCM), and immune privilege factor (EAE F7) on the severity of experimental allergic encephalitis (EAE) in rats. See text, Section 7, for details. EAE Control is no injections after immunization.

Figure 3:
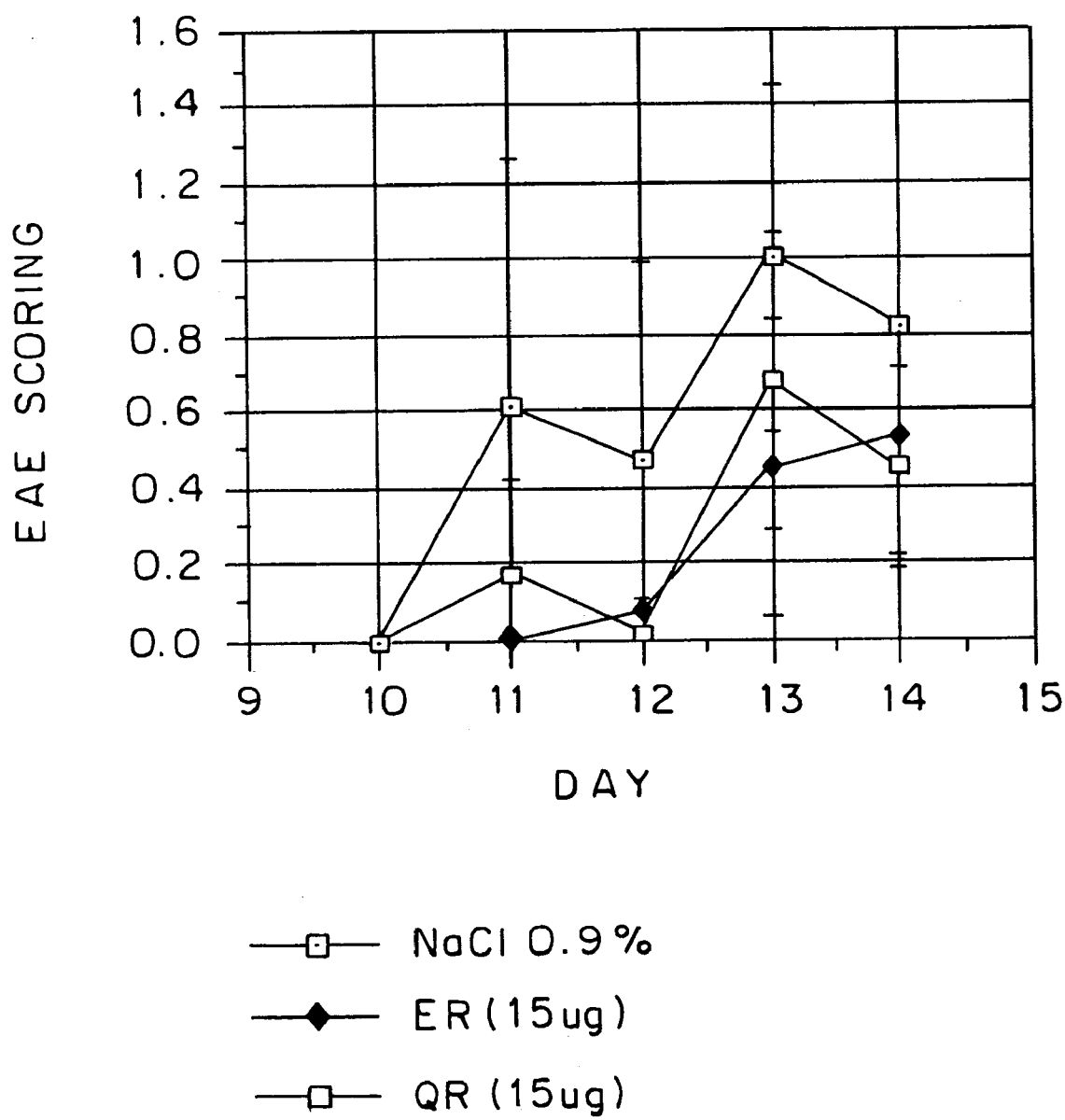

FIG. 3 is a graph showing the effect of saline (NaCl 0.9%), peptide Glu-Arg (ER) and peptide Gln-Arg (QR) on the severity of experimental allergic encephalitis (EAE) in rats. See text, Section 7, for details.

Figure 4:
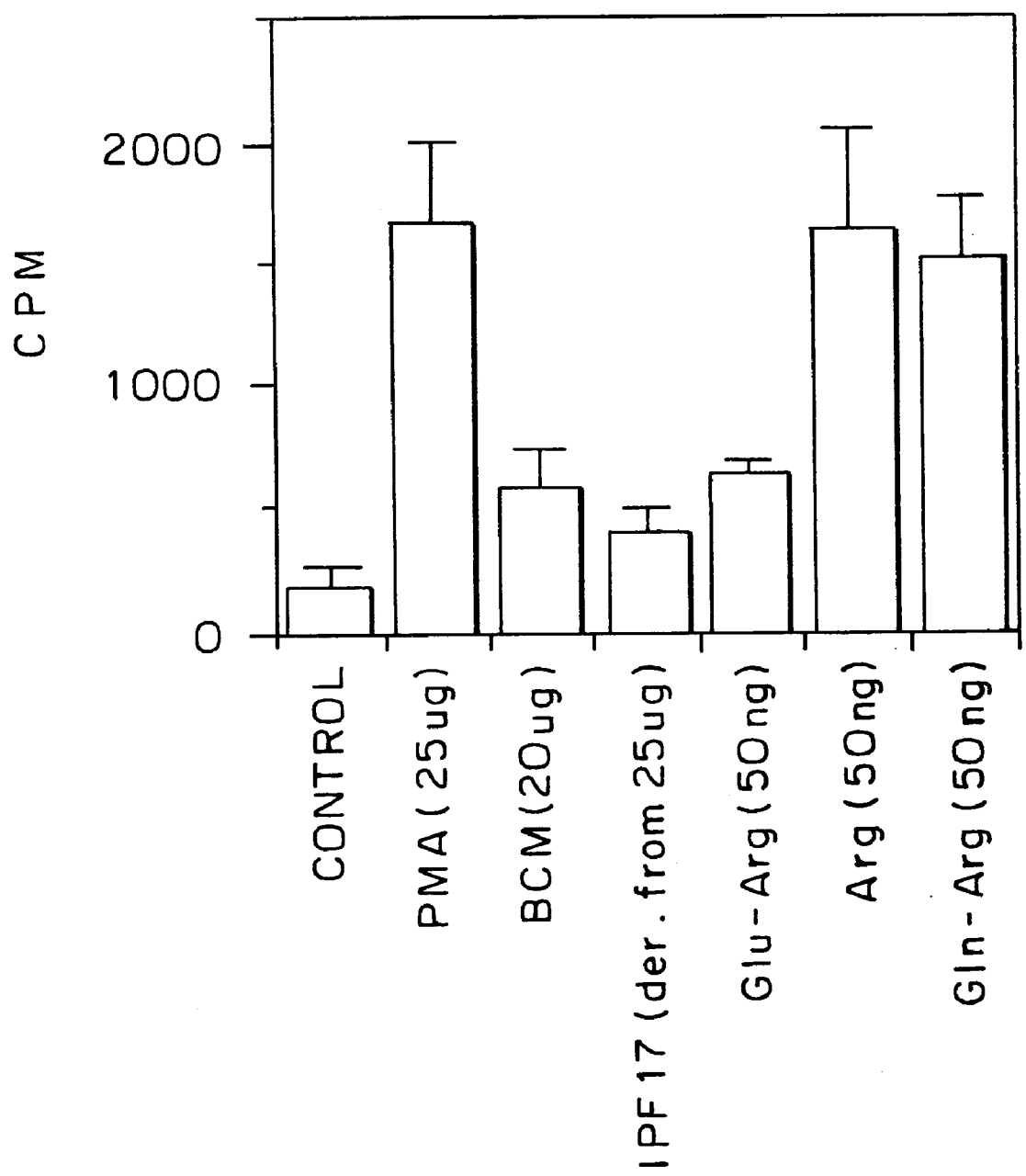

FIG. 4 is a bar graph showing the ability of the peptide Glu-Arg (ER) to inhibit T cell adhesion to extracellular matrix. Abbreviations: PMA, phorbol 12-myristate-13-acetate; BCM, brain conditioned medium; IPF f7, enriched immune privilege factor. See text, Section 8, for details.

Figure 5:
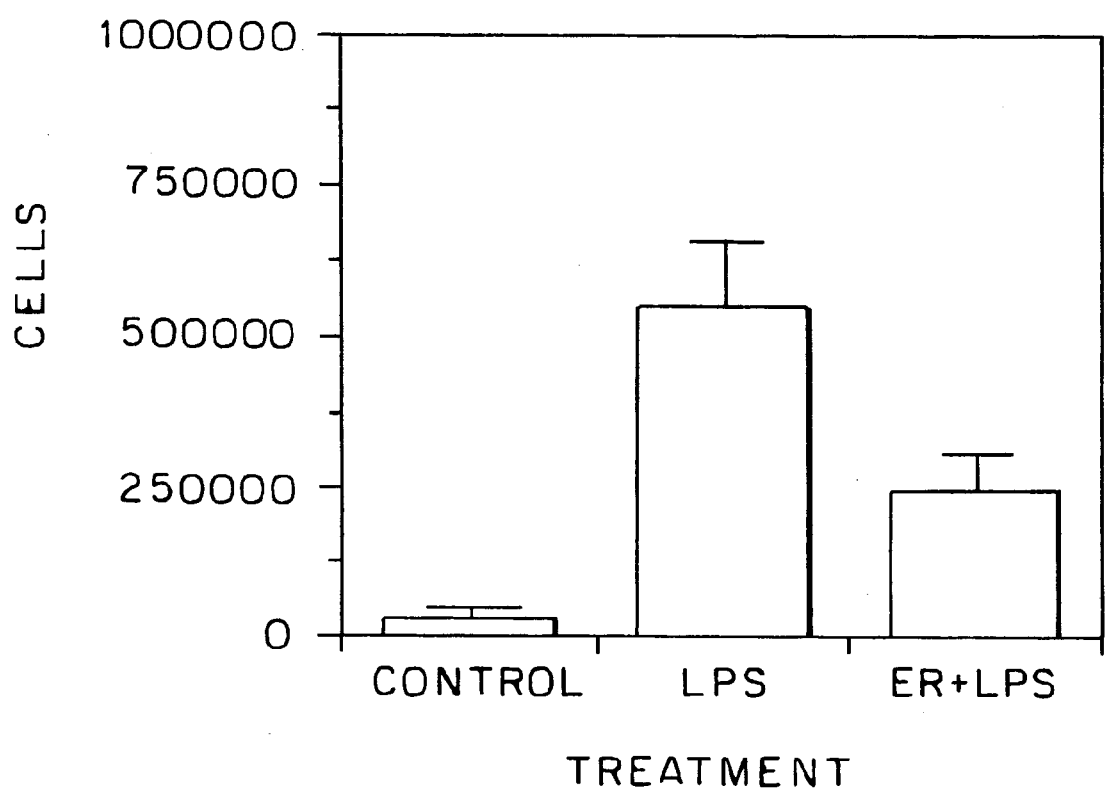

FIG. 5 is a bar graph showing the reduction in severity of uveitis in rat eye by administration of the peptide Glu-Arg (ER). See text, Section 9, for details.

5. DETAILED DESCRIPTION OF THE INVENTION

5.1. PEPTIDES AND PEPTIDE DERIVATIVES USEFUL AS ANTI-INFLANMATORY OR ANTI-IMMUNE RESPONSE AGENTS

The peptides, peptide derivatives and pharmaceutical compositions of the present invention have macrophage inhibitory and/or T cell inhibitory activity and thus, anti-inflammatory activity. The peptides and compositions have anti-immune activity, i.e., inhibitory effects against a cellular and/or humoral immune response, including a response not associated with inflammation. The peptides also inhibit the ability of macrophages and T cells to adhere to extracellular matrix components and fibronectin, as well as upregulate fas receptor expression in T cells.

As used herein, the term "peptide derivative" includes the derivatives defined in (v) to (ix) above, namely cyclic peptides, peptides obtained by substitution of a natural amino acid residue by the corresponding D-stereomer or by a non-natural amino acid residue, chemical derivatives of the peptides, dual peptides and multimers of the peptides.

The term "cyclic peptides" as used herein are cyclic derivatives of the peptides of (i) through (iv) to which two additional amino acid residues suitable for cyclization have been added, one at the carboxyl terminus and one at the amino terminus. Thus, the cyclic peptides contain either an intramolecular disulfide bond, i.e., —S—S—, an intramolecular amide bond between the two added residues, i.e., —CONH— or —NHCO— or intramolecular S-alkyl bonds, i.e., —S—$(CH_2)_n$—CONH— or —NH—CO$(CH_2)_n$—S—, wherein n is 1 or 2. In a preferred embodiment, the peptide Glu-Arg is derivatized by the incorporation of two terminal cysteine residues and cyclized through an intramolecular S—S bond between the two incorporated cysteine residues.

The cyclic derivatives containing an intramolecular disulfide bond may be prepared by conventional solid phase synthesis (Merrifield et al., 1982) while incorporating suitable S-protected cysteine or homocysteine residues at the positions selected for cyclization such as the amino and carboxyl termini (Sahm et al., 1996, J. Pharm. Pharmacol. 48(2):197). Following completion of the chain assembly, cyclization can be performed either by selective removal of the S-protecting groups with a consequent on-support oxidation of free corresponding two SH-functions, to form S—S bonds, followed by conventional removal of the product from the support and appropriate purification procedure, or by removal of the peptide from the support along with complete side-chain deprotection, followed by oxidation of the free SH-functions in highly dilute aqueous solution.

The cyclic derivatives containing an intramolecular amide bond may be prepared by conventional solid phase synthesis while incorporating suitable amino and carboxyl side-chain protected amino acid derivatives at the positions selected for cyclization. The cyclic derivatives containing intramolecular —S-alkyl bonds can be prepared by conventional solid phase synthesis while incorporating an amino acid residue with a suitable amino-protected side chain, and a suitable S-protected cysteine or homocysteine residue at the positions selected for cyclization.

According to another embodiment, a peptide of the invention has one or more of the amino acid residues replaced by the corresponding D-amino acid residue. Thus the peptide or peptide derivative of the invention may be all-L, all-D or a D,L-peptide. In another embodiment, an amino acid residue may be replaced by a non-natural amino acid residue provided that the charge of the peptide is not substantially changed. Examples of non-naturally occurring or derivatized non-naturally occurring amino acids include Na-methyl amino acids, Cα-methyl amino acids, β-methyl amino acids and amino acid analogs in general such as, but not being limited to, β-alanine (β-Ala), norvaline (Nva), norleucine (Nle), 4-aminobutyric acid (γ-Abu), 2-aminoisobutyric acid (Aib), 6-aminohexanoic acid (ε-Ahx), ornithine (Orn), hydroxyproline (Hyp), sarcosine, citrulline, cysteic acid, and cyclohexylalanine.

A chemical derivative of a peptide of the invention includes, but is not limited to, a derivative containing additional chemical moieties not normally a part of the peptide provided that the derivative retains the anti-inflammatory function of the peptide. Examples of such derivatives are: (a) N-acyl derivatives of the amino terminal or of another free amino group, wherein the acyl group may be either an alkanoyl group, e.g., acetyl, hexanoyl, octanoyl; an aroyl group, e.g., benzoyl, or a blocking group such as Fmoc (fluorenylmethyl-O—CO—), carbobenzoxy (benzyl-O—CO—-), monomethoxysuccinyl, naphthyl-NH—CO—, acetylamino-caproyl, adamantyl-NH—CO—; (b) esters of the carboxyl terminal or of another free carboxyl or hydroxy groups; (c) amides of the carboxyl terminal or of another free carboxyl groups produced by reaction with ammonia or with a suitable amine; (d) glycosylated derivatives; (e) phosphorylated derivatives; (f) derivatives conjugated to lipophilic moieties, e.g., caproyl, lauryl, stearoyl; and (g) derivatives conjugated to an antibody or other cellular ligands.

Also included among the chemical derivatives are those derivatives obtained by modification of the peptide bond —CO—NH—, for example, by (a) reduction to —CH$_2$—NH—; (b) alkylation to —CO—N (alkyl)-; (c) inversion to —NH—CO—.

A dual peptide according to the invention consists of two the same or different peptides of the invention covalently linked to one another or through a spacer such as by a short stretch of alanine residues or by a putative site for proteolysis by cathepsin (see U.S. Pat. No. 5,126,249 and European Patent No. 495,049 with respect to such sites). This will induce site-specific proteolysis of the preferred form into the two desired analogues. In a preferred embodiment the dual peptide is Glu-Arg-Glu-Arg (SEQ No:1).

Multimers according to the invention consist of polymer molecules formed from a number of the same or different peptides or derivatives thereof. The polymerization is carried out with a suitable polymerization agent, such as 0.1% glutaraldehyde (Audibert et al., 1981, Nature 289:593).

In one aspect of the invention, the peptide derivative is more resistant to proteolytic degradation than the corresponding nonderivatized peptide. For example, a peptide derivative having D-amino acid substitution(s) in place of a L-amino acid resists proteolytic cleavage when administered to a mammal. In another aspect of the invention, the peptide derivative has increased permeability across a cell membrane than the corresponding nonderivatized peptide, e.g., those peptide derivatives having a lipophilic moiety coupled at the amino and/or carboxyl terminus. In yet another aspect, the peptide derivative has enhanced biological activity, e.g., those peptide derivatives which are dualized or multimerized peptides.

The peptides or peptide derivatives of the present invention are obtained by any method of peptide synthesis known to those of skill in the art, including synthetic and recombinant techniques. For example, the peptides or peptide derivatives can be obtained by solid phase peptide synthesis, which, in brief, consists of coupling the carboxyl group of the C-terminal amino acid to a resin and successively adding N-alpha protected amino acids. The protecting groups may be any known in the art. Before each new amino acid is added to the growing chain, the protecting group of the previous amino acid added to the chain is removed. The coupling of amino acids to appropriate resins is described by Rivier et al., U.S. Pat. No. 4,244,946. Such solid phase syntheses have been described, for example, by Merrifield, 1964, *J. Am. Chem. Soc.* 85:2149; Vale et al. 1981, *Science* 213:1394–1397; Marki et al., 1981 *J. Am. Chem. Soc.* 103:3178 and in U.S. Pat. Nos. 4,305,872 and 4,316,891. In a preferred aspect, an automated peptide synthesizer is employed.

Purification of the synthesized peptides or peptide derivatives is carried out by standard methods including chromatography (e.g., ion exchange, affinity, and sizing column chromatography), centrifugation, differential solubility, hydrophobicity, or by any other standard technique for the purification of proteins. In a preferred embodiment, thin layer chromatography is employed.

The peptides, peptide derivatives and compositions comprising the same of the present invention have macrophage and/or T cell inhibitory activity.

As used herein, the term "macrophages" is intended to comprise, without limitation, macrophages obtained from any site, including any cavity or tissue, for example, macrophages obtained from serosal cavities such as the peritoneal or pleural cavity, alveolar macrophages, and macrophages associated with other tissues, where the macrophages may be known by various terms such as Kupffer cells (in the liver) and microglial cells (in the central nervous system).

Macrophage activities, such as migration, phagocytosis, adhesion and interleukin-1 (IL-1) production can be measured in in vitro assays. For example, an in vitro assay for measuring macrophage migration uses modified Boyden chambers wherein the bottom half of the chamber is separated from the upper half by a filter. The upper chamber contains macrophages isolated, e.g., from blood or derived from tissue culture. If the bottom chamber contains an inhibitor of macrophage migration then fewer macrophages will adhere to the filter separating the two halves of the Boyden chamber as compared to a control. In order to detect the macrophages on the filter, the macrophages can be labeled with any suitable marker (such as fluorescein or rhodamine), or a radioactive marker (such as a radioactive isotope of iodine, chromium, carbon, or hydrogen). Alternatively, the assay can be performed with unlabeled cells; the cells can be detected by any suitable method, such as microscopically, with or without staining. An in vitro macrophage migration assay is described in Hirschberg and Schwartz, 1995, J. Neuroimmunol. 61:89–96.

Another macrophage activity, phagocytosis, is measured in vitro by contacting the macrophages with labeled particles and subsequently determining the amount of label within the macrophages. A wide variety of particles can be used for this purpose, including but without limitation latex or polystyrene beads and naturally occurring cells, such as red blood cells, yeast and bacteria. Optionally, the particles can be opsonized, for example with immunoglobulin or complement. The particles can be labeled with any suitable marker (such as fluorescein or rhodamine), a radioactive marker (such as a radioactive isotope of iodine, carbon, or hydrogen), and an enzyme. Alternatively, the assay can be performed with unlabeled particles (e.g., red blood cells or yeast); the unlabeled particles are detected by any suitable method, such as microscopically, with or without staining. An in vitro assay for phagocytosis is described by Harvath and Terle, 1994, in: Methods for Molecular Biology, Vol. 34, L. C. Javois (ed.), Humana Press, Inc., Totowa, N.J.

Yet another macrophage activity, adhesion to fibronectin or extracellular matrix, is measured in vitro by incubating labeled macrophages in tissue culture plates that have been precoated with fibronectin or extracellular matrix, and determining the number of macrophages that adhere to the plate. The macrophages can be labeled with any suitable marker (such as fluorescein or rhodamine), or a radioactive marker (such as a radioactive isotope of iodine, chromium, carbon, or hydrogen). Alternatively, the assay can be performed with unlabeled cells; the adherent cells can be detected by any suitable method, such as microscopically, with or without staining. An in vitro adhesion assay is described in Gilat et al., 1994, J. Immunol. 153:4899.

T cell activities, such as adhesion to fibronectin or extracellular matrix, interleukin-2 (IL-2) production, etc., also can be measured in in vitro assays. An in vitro assay measuring T cell adhesion is described in Section 7, infra.

5.2. METHODS AND COMPOSITIONS FOR TREATING OR AMELIORATING INFLAMMATION OR FOR INHIBITING AN IMMUNE RESPONSE

The methods of the present invention comprise administering to a subject in need thereof an effective amount of a peptide, a peptide derivative or a composition comprising a peptide or peptide derivative to a subject to inhibit inflammation. In one embodiment, an effective amount of a therapeutic composition comprising a peptide and a pharmaceutical carrier is administered systemically to a subject to inhibit inflammation. In another embodiment, an effective amount of a therapeutic composition comprising a peptide and a pharmaceutical carrier is applied locally to a site to inhibit inflammation at the site. In one aspect of this embodiment, the site is a site of damage or unwanted inflammation in a joint. This damage or unwanted inflammation can be due to arthritis. In another aspect of this embodiment, the site is a site of nerve injury in the central nervous system.

The peptides, peptide derivatives and pharmaceutical compositions of the present invention are used in the treatment of or amelioration of inflammatory symptoms in any disease, condition or disorder where immune and/or inflammation suppression would be beneficial. Inflammatory diseases, conditions or disorders in which the peptides, peptide derivatives and compositions of the present invention can be used to inhibit unwanted immune reactions and inflammation include, but are not limited to, arthritis, including but not limited to rheumatoid arthritis, and other diseases, conditions or disorders of the joints or musculoskeletal system in which immune and/or inflammation suppression would be beneficial.

The peptides, peptide derivatives and compositions are also useful to treat or ameliorate inflammation associated with hypersensitivity; allergic reactions; asthma; systemic lupus erythematosus; collagen diseases and other autoimmune diseases, conditions or disorders in which immune and/or inflammation suppression would be beneficial.

Moreover, the peptides, peptide derivatives and compositions are also useful to treat or ameliorate inflammation associated with atherosclerosis; arteriosclerosis; atherosclerotic heart disease; reperfusion injury; cardiac arrest; myocardial infarction; vascular inflammatory disorders; respiratory distress syndrome and other cardiopulmonary diseases, conditions or disorders where immune and/or inflammation suppression would be beneficial.

In addition, the peptides, peptide derivatives and compositions are also useful to treat or ameliorate inflammation associated with peptic ulcer; ulcerative colitis and other diseases, conditions or disorders of the gastrointestinal tract where immune inflammation suppression would be beneficial; hepatic fibrosis; liver cirrhosis and other hepatic diseases, conditions or disorders where immune and/or inflammation suppression would be beneficial; thyroiditis and other glandular diseases, conditions or disorders where immune and/or inflammation suppression would be beneficial; glomerulonephritis and other renal and urologic diseases, conditions or disorders where immune and/or inflammation suppression would be beneficial.

The peptides, peptide derivatives and compositions are also useful to treat or ameliorate inflammation associated with otitis and other otorhinolaryngological diseases, conditions or disorders where immune and/or inflammation suppression would be beneficial; dermatitis and other dermal diseases, conditions or disorders where immune and/or inflammation suppression would be beneficial; periodontal diseases and other dental diseases, conditions or disorders where immune and/or inflammation suppression would be beneficial.

Further, the peptides, peptide derivatives and compositions are also useful to treat or ameliorate inflammation associated with orchitis and epididimo-orchitis; infertility; orchidal trauma and other immune-related testicular diseases, conditions or disorders where immune and/or inflammation suppression would be beneficial; placental dysfunction; placental insufficiency; habitual abortion; eclampsia; pre-eclampsia and other immune and/or inflammatory-related gynecological diseases, conditions or disorders where immune and/or inflammatory suppressions would be beneficial.

In addition, the peptides, peptide derivatives and compositions are also useful to treat or ameliorate inflammation associated with posterior uveitis; intermediate uveitis; anterior uveitis; conjunctivitis; chorioretinitis; uveoretinitis; optic neuritis; intraocular inflammation, such as retinitis and cystoid macular edema; sympathetic ophthalmia; scleritis; retinitis pigmentosa; immune and inflammatory components of degenerative fondus disease; inflammatory components of ocular trauma; ocular inflammation caused by infection; proliferative vitreoretinopathies; acute ischemic optic neuropathy; excessive scarring, for example, following glaucoma filtration operation; immune and/or inflammation reaction against ocular implants and other immune and inflammatory-related ophthalmic diseases, conditions or disorders where immune and/or inflammation suppression would be beneficial.

Moreover, the peptides, peptide derivatives and compositions are also useful to treat or ameliorate inflammation associated with autoimmune diseases and conditions or disorders where, both in the central nervous system (CNS) and in any other organ, immune and/or inflammation suppression would be beneficial; Parkinson's disease; complications and/or side effects from treatment of Parkinson's disease; AIDS-related dementia complex (HIV-related encephalopathy); Devic's disease; Sydenham chorea; Alzheimer's disease and other degenerative diseases, conditions or disorders of the central nervous system where immune and/or inflammation suppression would be beneficial; inflammatory components of strokes; post-polio syndrome; immune and inflammatory components of psychiatric disorders; myelitis; encephalitis; subacute sclerosing panencephalitis; encephalomyelitis; acute neuropathy; subacute neuropathy; chronic neuropathy; Guillaim-Barre syndrome; Sydenham chorea; myasthenia gravis; pseudotumor cerebri; Down's syndrome; Huntington's disease; amyotrophic lateral sclerosis; inflammatory components of central nervous system (CNS) compression or CNS trauma or infections of the CNS; inflammatory components of muscular atrophies and dystrophies; and immune and inflammatory related diseases, conditions or disorders of the central and peripheral nervous systems where immune and/or inflammation suppression would be beneficial.

In addition, the peptides, peptide derivatives and compositions are also useful to treat or ameliorate inflammation associated with post-traumatic inflammation; septic shock; infectious diseases where immune and/or inflammation suppression would be beneficial; inflammatory complications and side effects of surgery where immune and/or inflammation suppression would be beneficial; bone marrow transplantation and other transplantation complications and/or side effects where immune and/or inflammation suppression would be beneficial; inflammatory and/or immune complications and side effects of gene therapy, e.g., due to infection with a viral carrier; and inflammation associated with acquired immune deficiency syndrome (AIDS).

Further, the peptides, peptide derivatives and compositions are also useful to inhibit macrophage or T cell associated aspects of an immune response that are not associated with inflammation. The peptides and peptide derivatives are able to inhibit macrophage or T cell activities including, but not limited to, macrophage antigen-presenting activity, macrophage cytokine production, T cell cytokine production, T cell adhesion activity, T cell proliferation, etc. Thus, the peptides, peptide derivatives and compositions are useful to suppress or inhibit a humoral and/or cellular immune response.

The peptides, peptide derivatives and compositions are also useful to treat or ameliorate monocyte and leukocyte proliferative diseases, e.g., leukemia, by reducing the amount of monocytes and lymphocytes.

The peptides, peptide derivatives and pharmaceutical compositions of the invention are further useful for the prevention and/or treatment of graft rejection in cases of transplantation of natural or artificial cells, tissue and organs, such as cornea, bone marrow, organs, lenses, pacemakers, natural and artificial skin tissue, and the like.

The methods of the present invention also provide for the treatment of a subject in need of such treatment to reduce inflammation by administration of a therapeutic composition comprising a peptide or peptide derivative of the present invention and a pharmaceutically acceptable carrier. The subject is preferably an animal, including but not limited to animals such as cows, sheep, pigs, chickens, etc., and is preferably a mammal, and most preferably a human.

The methods of the present invention also provide for the treatment of a subject in need of such treatment to inhibit a humoral and/or cellular immune response by administration of a therapeutic composition comprising a peptide or peptide derivative of the present invention and a pharmaceutically acceptable carrier. The subject is preferably an animal, including but not limited to animals such as cows, pigs, chickens, etc., and is preferably a mammal, and most preferably a human.

The methods of the present invention also provide for the treatment of a subject in need of such treatment to restore immune privilege at an immune privileged site which has lost its immune privilege by administration of a therapeutic composition comprising a peptide or peptide derivative of the present invention and a pharmaceutically acceptable carrier. The subject is preferably an animal, including but not limited to animals such as cows, pigs, chickens, etc., and is preferably a mammal, and most preferably a human.

An immune privileged site is defined as a site at which a graft of foreign tissue, that would be rejected promptly if placed at a conventional body site, enjoys prolonged, even indefinite, survival. The list of sites has been determined experimentally and includes the anterior chamber of the eye, the corneal stroma of the eye, the central nervous system, including the brain, the maternal-fetal interface, the adrenal cortex, the testes, the ovaries, the liver, the matrix of hair follicles, and the vitreous cavity of the eye.

Various delivery systems are known and can be used to administer a peptide, peptide derivative or a composition of the invention. For example, the pharmaceutical compositions of the present invention can be administered systemically by, e.g., intravenous or intramuscular injection. In another example, the pharmaceutical compositions of the invention can be introduced to a site which is a joint by any suitable route including intravenously, sub-cutaneously, orally, trans-cutaneously, topically, intramuscularly, intraarticularly, retrobulbarly, subconjunctivally, etc. In yet another example, the pharmaceutical compositions of the invention can be introduced into the central nervous system by any suitable route, including intraventricular and intrathecal injection, etc. Intraventricular injection may be facilitated by an intraventricular catheter, for example, attached to a reservoir, such as an Ommaya reservoir. For veterinary purposes the composition may be administered intraperitoneally.

In a specific embodiment, the therapeutic or pharmaceutical compositions of the invention are administered locally to the area in need of treatment. This may be achieved by, for example, and not by way of limitation, local infusion during surgery, topical application, e.g., cream, ointment, in conjunction with a wound dressing after surgery or directly onto the eye, by injection, by means of a catheter, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue. In another embodiment, the therapeutic or pharmaceutical composition can be administered to the eye by eye drops.

In yet another embodiment, the therapeutic or pharmaceutical composition can be delivered in a vesicle, in particular, a liposome see Langer, 1990, Science 249:1527–1533; Treat et al., 1989, in Liposomes in the Therapy of Infectious Disease and Cancer, Lopez-Berestein and Fidler (eds.), Liss, N.Y., pp. 353–365; Lopez-Berestein, ibid., pp. 317–327; see generally ibid.)

In yet another embodiment, the therapeutic or pharmaceutical composition can be delivered in a controlled release system. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise, 1974, (eds.), CRC Pres., Boca Raton, Fla.; Controlled Drug Bioavailability, Drug Product Design and Performance, Smolen and Ball (eds.), 1984, Wiley, N.Y.; Ranger and Peppas, 1983, J. Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the therapeutic target, i.e., the brain (see, e.g., Goodson, 1984, in Medical Applications of Controlled Release, supra, vol. 2, pp. 115–138).

Other controlled release systems are discussed in the review by Langer, 1990, Science 249:1527–1533.

The present invention also provides for therapeutic or pharmaceutical compositions comprising a peptide or a peptide derivative of the invention in a form which can be combined with or in combination with a pharmaceutically acceptable carrier, which compositions can be administered as described above. The term "carrier" refers to a diluent, adjuvant, excipient, or vehicle with which the peptide is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers, particularly for injectable solutions. Particularly preferred pharmaceutical carriers for treatment of or amelioration of inflammation in the central nervous system are carriers that can penetrate the blood/brain barrier.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The therapeutic composition, if desired, can also contain minor amounts of wetting or emulsifying agents, or pH buffering agents. These compositions can take the form of solutions, suspensions, emulsion, tablets, capsules, powders, sustained-release formulations and the like. The composition can be formulated with traditional binders and carriers such as triglycerides.

Examples of suitable pharmaceutical carriers are described in "Remington's Pharmaceutical Sciences" by E. W. Martin. Such compositions contain a therapeutically effective amount of the therapeutic composition, together with a suitable amount of carrier so as to provide the form for proper administration to the patient. The formulation should suit the mode of administration.

In a preferred embodiment, the composition is formulated in accordance with routine procedures as a pharmaceutical composition adapted for local injection administration to human beings. Typically, compositions for local injection administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is administered by injection, an ampoule of sterile water for injection or saline can be provided so that the ingredients may be mixed prior to administration.

The therapeutic or pharmaceutical compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The present invention also provides for the modification of the peptide or peptide derivative such that it is more stable once administered to a subject, i.e., once administered it has a longer time period of effectiveness as compared to unmodified peptide. Such modifications are well know to those of skill in the art, e.g., polyethylene glycol derivatization (PEGylation), microencapsulation, etc.

The amount of the therapeutic or pharmaceutical composition of the invention which is effective in the treatment of a particular disease, condition or disorder will depend on the nature of the disease, condition or disorder and can be determined by standard clinical techniques. In general, the dosage ranges from about 0.001 mg/kg to about 2 mg/kg. In addition, in vitro assays may optionally be employed to help identify optimal dosage ranges. The precise dose to be employed in the formulation will also depend on the route of administration, and the seriousness of the disease, condition or disorder, and should be decided according to the judgment of the practitioner and each patient's circumstances. Effective doses may be extrapolated from dose-response curves derived from in vitro or animal model test systems. For example, in order to obtain an effective mg/kg dose for humans based on data generated from rat studies, the effective mg/kg dosage in rats is divided by six.

The invention also provides a pharmaceutical pack or kit comprising one or more containers filled with one or more of the ingredients, i.e., peptide, carrier, of the pharmaceutical compositions of the invention.

The following series of examples are presented by way of illustration and not by way of limitation on the scope of the invention.

6. EXAMPLE: MIGRATION PATTERN OF IMMUNE PRIVILEGE FACTOR AND PEPTIDE GLU-ARG IS THE SAME

In order to determine if the immune privilege factor and the peptide Glu-Arg have a similar migration pattern, the two compounds were subjected to a comparison on a thin-layer chromatography (TLC) plate.

A composition containing Immune Privilege Factor (IPF) in enriched form was obtained by subjecting brain conditioned medium obtained by incubating brain tissue in DMEM tissue culture medium to gel filtration chromatography using a SUPERDEX™ 75 column (a gel filtration medium, Pharmacia, Uppsala, Sweden). The flow rate through the column was 0.5 ml/minute, the running buffer was 50 mM $NH_4HCO_3$ and the fractions were collected as 2.5 ml aliquots. The fractions which retained the ability to inhibit macrophage migration were combined and designated IPF f7 or enriched IPF.

A composition containing purified IPF was obtained by subjecting IPF f7 obtained above to reverse phase high pressure liquid chromatography (HPLC). IPF f7 was run over a C-18 column with 5 $\mu$m pores and the gradient was run with 0–30% acetonitrile in double distilled water for 30 minutes with a flow rate of 0.8 ml per minute. The fractions containing the purified IPF had an elution time of 9 to 17 minutes.

A peptide having the amino acid sequence glutamic acid-arginine (Glu-Arg) was synthesized and subjected to thin layer chromatography (TLC) on a silica gel 60 pre-coated plastic foil plate (Merck, Rahway, N.J.) using butanol:acetic acid:pyridine:urate (15:13:10:3) as the running buffer. The peptide was excised and extracted from the silica gel into double distilled water. Amino acids glutamine and arginine were obtained from Sigma Chemical, Co., St. Louis, Mo.

The amino acids glutamine and arginine, the peptide Glu-Arg, the hydrochloric salt of peptide Glu-Arg, enriched IPF and purified IPF were subjected to thin-layer chromatography on a silica gel 60 precoated plastic foil plate (Merck, Rahway, N.J.) using butanol:acetic acid:pyridine:double distilled water (15:3:10:12) as the running buffer. The TLC plate was stained to visualize the peptides and amino acids. The results are shown in FIG. 1.

FIG. 1 clearly shows that Glu-Arg, enriched, and purified immune privilege factor have a similar migration pattern.

7. EXAMPLE: DELAY IN ONSET AND REDUCTION OF SEVERITY AND INCIDENCE OF ACUTE EXPERIMENTAL ACUTE ENCEPHALITIS

Multiple sclerosis is the major demyelinating disease affecting the central nervous system in humans. Experimental allergic encephalitis is induced by immunization of susceptible animals with myelin proteins and serves as an animal model for multiple sclerosis. (For a general review of multiple sclerosis and experimental allergic encephalitis, see Martin et al., 1992, Ann. Rev. Immunol. 10:153–187). The ability of the peptides of the present invention, brain conditioned medium, and immune privilege factor to delay the onset and reduce the severity of experimental allergic encephalitis was determined as follows.

Brain conditioned medium (BCM) was obtained as follows: 12–14 week old female Lewis rats were over-anesthetized with chloroform and brain tissue was aseptically removed and placed in cold PBS. The tissue was cleaned of debris and subsequently incubated in DMEM tissue culture medium for 24 hours at 37° C., 5% $CO_2$, 95% relative humidity.

A composition containing Immune Privilege Factor (IPF) in enriched form was obtained by subjecting the brain conditioned medium obtained above to gel filtration chromatography using a SUPERDEX™ 75 column (a gel filtration medium, Pharmacia, Uppsala, Sweden). The flow rate through the column was 0.5 ml/minute, the running buffer was 50 mM $NH_4HCO_3$ and the fractions were collected as 2.5 ml aliquots. The fractions which retained the ability to inhibit macrophage migration were combined and designated F7.

Peptides having the amino acid sequence glutamic acid-arginine (Glu-Arg) and glutamine-arginine (Gln-Arg) were synthesized and subjected to thin layer chromatography (TLC) on a silica gel 60 precoated plastic foil plate (Merck, Rahway, N.J.) using butanol:acetic acid:pyridine:urate (15:13:10:3) as the running buffer. The peptides were excised and extracted from the silica gel into double distilled water.

Female Lewis rats, which are genetically susceptible to multiple sclerosis, were injected intradermally with 100 µg of a fragment of myelin basic protein (amino acid residues 68–88) (MBP) (see, Chou et al., 1977, J. Neurobiol. 28:115) isolated from guinea pig spinal cord and mixed with Freund's complete adjuvant. Three days post-injection of MBP, the rats were injected, intraperitoneally, daily with saline, BCM, IPF (equivalent to 15 µg of peptide Glu-Arg), peptide Glu-Arg (15 µg), or peptide Gln-Arg (15 µg) and the severity of the induced encephalitis was measured by scoring for the severity of observed paralysis as described in Chou et al., 1977, J.

Neurobiol. 28:115. The higher the score, the more severe the paralysis. EAE Control is no injections after immunization. The results are shown in FIGS. 2 and 3 and in Table I.

TABLE I

|  | CONTROL | NaCl | BCM | F7 |
|---|---|---|---|---|
| Incidence of Sick Animal (Day 13) | 100% | 100% | 30% | 0% |
| Severity of Disease (Day 13) | 2.25 (±0.94) | 2.25 (±0.75) | 0.33 (±0.33) | 0 (±0) |
| Day of Onset of Disease | 10 (±0) | 11.5 (±0.7) | 12.6 (±2.0) | 14 (±0) |

FIGS. 2 and 3 clearly show that BCM, F7, Glu-Arg, and Gln-Arg are able to delay the time of onset and reduce the severity of experimental allergic encephalitis. Table I shows that F7 also reduces the incidence of experimental allergic encephalitis.

8. EXAMPLE: INHIBITION OF T CELL ADHESION

Two peptides, one having the amino acid sequence glutamic acid-arginine (Glu-Arg) and the other glutamine-arginine (Gln-Arg), were synthesized and subjected to thin layer chromatography (TLC) on a silica gel 60 precoated plastic foil plate (Merck, Rahway, N.J.) using butanol:acetic acid:pyridine:urate (15:13:10:3) as the running buffer. The peptides were excised and extracted from the silica gel into double distilled water.

The peptides, Glu-Arg and Gln-Arg, along with brain conditioned medium (BCM) and immune privilege factor prepared as described in Section 7 (IPF f7), and the amino acid arginine, were tested for their ability to inhibit the adhesion of T cells to an extracellular matrix as follows.

Blood was obtained from healthy human donors and T cells were isolated by diluting the blood 1:1 with PBS and then centrifuging the dilutant through a Ficoll gradient for 20 minutes at 700×g to collect the mononuclear interphase. The monocytes were then excluded by filtering the interphase through nylon wool tubes (Uni-Sorb tubes, NovaMed, Israel). The purified T cells were centrifuged again for 15 minutes at 350×g. The pellet was resuspended in RPMI medium at $10^6$ cells per ml.

The isolated T cells were labeled with chromium[51] and added to 96 well plates precoated with fibronectin or retinal extracellular matrix in RPMI 1640 medium supplemented with 2% bovine serum albumin, 1 mM $Ca^{2+}$, 1 mm $Mg^{2+}$ 1% sodium pyruvate, 1% glucose and 1% HEPES buffer pH 7.0–7.4 (adhesion medium) at $10^5$ cells per 100 ml adhesion medium. The labeled T cells were preincubated with peptide Glu-Arg or Gln-Arg or preincubated with BCM or IPF f7 or with arginine for 60 minutes at 37° C., 5% $CO_2$, 95% relative humidity. After incubation the T cells were activated with 25 ng/well PMA. The wells were then washed 3 times to remove non-adherent cells. Radiolabelled adherent T cells were examined through an optical microscope to ensure cell viability and adequate washings. The cells were then lysed overnight with 1 M NaOH and the supernatants collected for gamma counting. PMA-free medium served as the control. The results of this experiment are shown in FIG. 4.

FIG. 4 clearly demonstrates that Glu-Arg, BCM and IPF f7 inhibit T cell adhesion to extracellular matrix.

9. EXAMPLE: REDUCTION IN SEVERITY OF LPB-INDUCED UVEITIS BY PEPTIDE GLU-ARG

The ability of the peptide Glu-Arg to reduce the severity of induced uveitis, an inflammatory disorder of the eye, as measured by the number of invading lymphocytes, was determined as follows. Albino NZ rabbits were injected with either 10 µg lipopolysaccharide (LPS) or were injected simultaneously with 10 µg LPS and 200 µg peptide Glu-Arg (in 50 µl saline) in the posterior chamber of the eye. The peptide Glu-Arg was synthesized as above in Section 8, control animals received injections of saline. The degree of uveitis was measured by counting the number of invading lymphocytes. The results are presented in FIG. 5.

FIG. 5 clearly shows that Glu-Arg was able to decrease the number of invading lymphocytes in response to LPS, thus reducing the severity of induced uveitis.

The invention claimed and described herein is not to be limited in scope by the specific embodiments herein disclosed since these embodiments are intended as illustrations of several aspects of the invention. Indeed, various modifications of the invention in addition to those shown and described herein will become apparent to those skilled in the art from the foregoing description. Such modifications are also intended to fall within the scope of the appended claims.

A number of references are cited herein, the entire disclosures of which are incorporated herein, in their entirety, by reference.

What is claimed is:

1. A substantially pure anti-inflammatory dipeptide consisting of the sequence of Glu-Arg.

2. A pharmaceutical composition comprising a pharmaceutically acceptable carrier and an anti-inflammatory dipeptide according to claim 1.

3. A pharmaceutical composition comprising a pharmaceutically acceptable carrier and an anti-inflammatory dipeptide according to claim 1, which composition inhibits macrophage activity and has macrophage migration and/or macrophage phagocytic inhibitory activity as assessed in an in vitro assay.

4. The pharmaceutical composition according to claim 2 which composition inhibits T cell activity and has T cell inhibitory activity as assessed in an in vitro assay.

* * * * *